(12) United States Patent
Fujita et al.

(10) Patent No.: US 11,414,381 B2
(45) Date of Patent: Aug. 16, 2022

(54) FLUORINATED IMIDE SALT COMPOUND AND SURFACTANT

(71) Applicants: Mitsubishi Materials Electronic Chemicals Co., Ltd., Akita (JP); Merck Patent GmbH, Darmstadt (DE)

(72) Inventors: Masato Fujita, Akita (JP); Takeshi Kamiya, Akita (JP); Kazuma Yamamoto, Kakegawa (JP)

(73) Assignees: Mitsubishi Materials Electronic Chemicals Co., Ltd., Akita (JP); Merck Patent GmbH, Darmstadt (DE)

( * ) Notice: Subject to any disclaimer, the term of this patent is extended or adjusted under 35 U.S.C. 154(b) by 0 days.

(21) Appl. No.: 17/278,414

(22) PCT Filed: Aug. 1, 2019

(86) PCT No.: PCT/JP2019/030158
§ 371 (c)(1),
(2) Date: Mar. 22, 2021

(87) PCT Pub. No.: WO2020/084854
PCT Pub. Date: Apr. 30, 2020

(65) Prior Publication Data
US 2021/0355080 A1    Nov. 18, 2021

(30) Foreign Application Priority Data

Oct. 24, 2018  (JP) ................ JP2018-200316

(51) Int. Cl.
*C07C 311/51* (2006.01)
*C09K 23/00* (2022.01)

(52) U.S. Cl.
CPC ............ *C07C 311/51* (2013.01); *C09K 23/00* (2022.01)

(58) Field of Classification Search
None
See application file for complete search history.

(56) References Cited

FOREIGN PATENT DOCUMENTS

| CA | 2096816 A1 | 11/1993 |
| JP | 06-116229 A | 4/1994 |
| JP | 2006206456 | * 8/2006 |
| JP | 2006210022 | * 8/2006 |
| JP | 4080998 B | 4/2008 |
| WO | WO-2018/095885 A1 | 5/2018 |

OTHER PUBLICATIONS

International Search Report dated Oct. 8, 2019 for the corresponding PCT International Patent Application No. PCT/JP2019/030158.

* cited by examiner

*Primary Examiner* — Amy C Bonaparte
(74) *Attorney, Agent, or Firm* — Leason Ellis LLP

(57) ABSTRACT

A fluorinated imide salt compound of the present invention is a compound represented by General Formula (1). In General Formula (1), m represents 1 or 2, n represents an integer from 1 to 4, α represents 1 or 2, and $X^{\alpha+}$ represents an α-valent metal ion, a primary ammonium ion, a secondary ammonium ion, a tertiary ammonium ion, a quaternary ammonium ion, or $NH_4^+$.

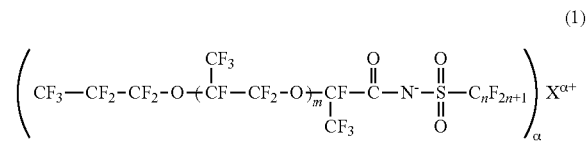

(1)

6 Claims, No Drawings

FLUORINATED IMIDE SALT COMPOUND AND SURFACTANT

CROSS-REFERENCE TO RELATED PATENT APPLICATIONS

This application is a U.S. National Phase Application under 35 U.S.C. § 371 of International Patent Application No. PCT/JP2019/030158 filed on Aug. 1, 2019 and claims the benefit of priority to Japanese Patent Application No. 2018-200316 filed on Oct. 24, 2018, all of which are incorporated herein by reference in their entirety. The International Application was published in Japanese on Apr. 30, 2020 as International Publication No. WO/2020/084854 under PCT Article 21(2).

FIELD OF THE INVENTION

The present invention relates to a fluorinated imide salt compound and a surfactant.

BACKGROUND OF THE INVENTION

Fluorinated compounds having a perfluoroalkyl group are widely used as fluorine-based surfactants because these compounds have excellent surface activity. As the fluorine-based surfactants, perfluorooctanoic acid (PFOA) and perfluorooctanesulfonic acid (PFOS) are known. In recent years, it has been revealed that compounds containing a linear perfluoroalkyl group having 7 or more carbon atoms are highly toxic and highly bioaccumulative. Therefore, the use of PFOA or PFOS has been restricted. Accordingly, surfactants as alternative materials for PFOA and PFOS have been in development.

Japanese Patent No. 4080998 discloses ammonium bis(perfluorobutanesulfonyl)imide: $NH_4^+\,^-N(SO_2C_4F_9)_2$. According to Japanese Patent No. 4080998, the ammonium bis(perfluorobutanesulfonyl)imide is more able to reduce surface tension than the ammonium salt of perfluorooctanoic acid (PFOA).

In PCT International Publication No. WO2018/095885, as a surfactant to be added to a lithography composition used for manufacturing a semiconductor integrated circuit, a flat panel display (FPD), a circuit board, a color filter, and the like, a fluorinated imide compound containing a fluorocarbon group having 5 or less carbon atoms is disclosed.

CITATION LIST

Patent Literature

[Patent Literature 1]
Japanese Patent No. 4080998
[Patent Literature 2]
PCT International Publication No. WO2018/095885

Technical Problem

Ammonium bis(perfluorobutanesulfonyl)imide disclosed in Japanese Patent No. 4080998 is more able to reduce surface tension than PFOA. However, according to the study conducted by the inventors of the present invention, the surface tension-reducing ability of the ammonium bis(perfluorobutanesulfonyl)imide is lower than that of PFOS, and needs to be further improved. Furthermore, the fluorinated imide compound disclosed in PCT International Publication No. WO2018/095885 tends to be easily hydrolyzed in water and to exhibit low stability in water.

The present invention has been made in consideration of the above circumstances, and an object thereof is to provide a novel compound and a surfactant that do not contain a linear perfluoroalkyl group having 7 or more carbon atoms, has a high surface tension-reducing ability, and exhibit excellent stability in water.

SUMMARY OF THE INVENTION

Solution to Problem

A compound of the present invention for achieving the above object is a fluorinated imide salt compound represented by General Formula (1).

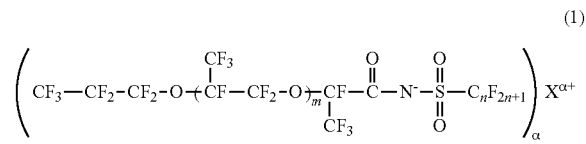

In General Formula (1), m represents 1 or 2, n represents an integer from 1 to 4, α represents 1 or 2, and $X^{\alpha+}$ represents an α-valent metal ion, a primary ammonium ion, a secondary ammonium ion, a tertiary ammonium ion, a quaternary ammonium ion, or $NH_4^+$.

The fluorinated imide salt compound of the present invention contains a metal ion, a primary ammonium ion, a secondary ammonium ion, a tertiary ammonium ion, a quaternary ammonium ion, or $NH_4^+$, and has an imide structure having high ion dissociation properties. Therefore, this compound is highly hydrophilic. Furthermore, this compound has a salt structure. Therefore, the compound is more stable in water and can be easily used for various uses. In addition, the compound has a structure in which an oxyperfluoropropyl group: $[CF_3-CF_2-CF_2-O-]$ is bonded to a carboxylic acid group of imide through an oxyperfluoropropylene group: $[-CF(CF_3)-CF_2-O-]$, and a perfluoroalkyl group having 4 or less carbon atoms is directly bonded to a sulfonic acid group of imide. Therefore, the compound is highly hydrophobic and highly lipophobic. Accordingly, the fluorinated imide salt compound of the present invention has high solubility in an aqueous solvent or an organic solvent, exhibits excellent stability in water, and has a high surface tension-reducing ability.

The compound of the present invention may be a fluorinated imide salt compound represented by General Formula (2).

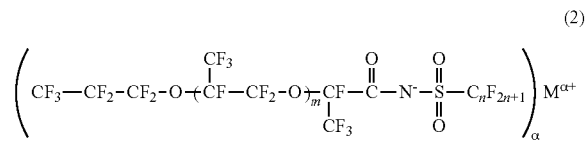

In General Formula (2), m represents 1 or 2, n represents an integer from 1 to 4, α represents 1 or 2, and $M^{\alpha+}$ represents an α-valent metal ion, a primary ammonium ion, a secondary ammonium ion, a tertiary ammonium ion, or a quaternary ammonium ion.

The fluorinated imide salt compound of the present invention contains a metal ion, a primary ammonium ion, a secondary ammonium ion, a tertiary ammonium ion, or a quaternary ammonium ion, and has an imide structure having high ion dissociation properties. Therefore, this compound is highly hydrophilic. Furthermore, this compound has a salt structure. Therefore, the compound is more stable in water and can be easily used for various uses. In addition, the compound has a structure in which an oxyperfluoropropyl group: [$CF_3$—$CF_2$—$CF_2$—O—] is bonded to a carboxylic acid group of imide through an oxyperfluoropropylene group: [—$CF(CF_3)$—$CF_2$—O—], and a perfluoroalkyl group having 4 or less carbon atoms is directly bonded to a sulfonic acid group of imide. Therefore, the compound is highly hydrophobic and highly lipophobic. Accordingly, the fluorinated imide salt compound of the present invention has high solubility in an aqueous solvent or an organic solvent, exhibits excellent stability in water, and has a high surface tension-reducing ability.

The compound of the present invention may be a fluorinated imide salt compound represented by General Formula (3).

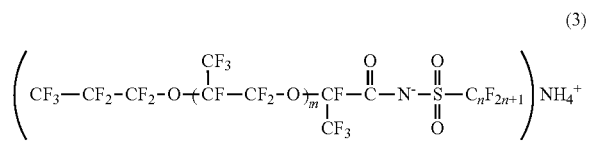

In General Formula (3), m represents 1 or 2, and n represents an integer from 1 to 4.

The fluorinated imide salt compound of the present invention contains an ammonium ion and has an imide structure having high ion dissociation properties. Therefore, this compound is highly hydrophilic. Furthermore, this compound has an ammonium salt structure. Therefore, this compound is more stable in water and can be easily used for various uses. This compound is highly hydrophilic and exhibits high stability in water. In addition, the compound has a structure in which an oxyperfluoropropyl group is bonded to a carboxylic acid group of imide through an oxyperfluoropropylene group, and a perfluoroalkyl group having 4 or less carbon atoms is directly bonded to a sulfonic acid group of imide. Therefore, the compound is highly hydrophobic and highly lipophobic. Accordingly, the fluorinated imide salt compound of the present invention has high solubility in an aqueous solvent or an organic solvent, exhibits excellent stability in water, and has a high surface tension-reducing ability.

A surfactant of the present invention contains the fluorinated imide salt compound described above.

Because the surfactant of the present invention contains the fluorinated imide salt compound described above, the surfactant has a high surface tension-reducing ability.

Advantageous Effects of Invention

According to the present invention, it is possible to provide a novel compound and a surfactant that do not contain a linear perfluoroalkyl group having 7 or more carbon atoms, have a high surface tension-reducing ability, and exhibit excellent stability in water.

DETAILED DESCRIPTION OF THE INVENTION

Hereinafter, the fluorinated imide salt compound and the surfactant according to embodiments of the present invention will be described.

<Fluorinated Imide Salt Compound>

The fluorinated imide salt compound according to an embodiment of the present invention is a compound represented by General Formula (1).

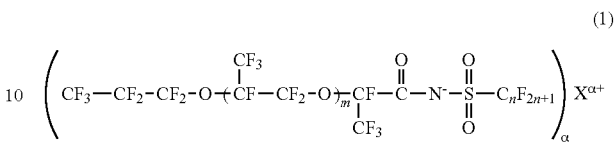

In General Formula (1), m represents 1 or 2, n represents an integer from 1 to 4, α represents 1 or 2, and $X^{\alpha+}$ represents an α-valent metal ion, a primary ammonium ion, a secondary ammonium ion, a tertiary ammonium ion, a quaternary ammonium ion, or $NH_4^+$.

According to a first embodiment of the present invention, the fluorinated imide salt compound represented by General Formula (1) is a compound in which α represents 1 or 2, and $X^{\alpha+}$ represents an α-valent metal ion, a primary ammonium ion, a secondary ammonium ion, a tertiary ammonium ion, or a quaternary ammonium ion. According to a second embodiment of the present invention, the fluorinated imide salt compound represented by General Formula (1) is a compound in which α represents 1, and $X^{\alpha+}$ represents $NH_4^+$. Hereinafter, the first embodiment and the second embodiment will be described.

First Embodiment

The fluorinated imide salt compound according to the first embodiment of the present invention is a compound represented by General Formula (2).

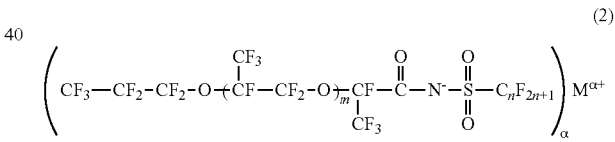

In General Formula (2), m represents 1 or 2, n represents an integer from 1 to 4, α represents 1 or 2, and $M^{\alpha+}$ represents an α-valent metal ion, a primary ammonium ion, a secondary ammonium ion, a tertiary ammonium ion, or a quaternary ammonium ion.

The fluorinated imide salt compound represented by General Formula (2) has a structure in which m represents 1 or 2, and an oxyperfluoropropyl group is bonded to a carboxylic acid group of imide through an oxy perfluoropropylene group. Therefore, this compound has higher hydrophobicity and higher lipophobicity. In a case where m is 0, the hydrophobicity and lipophobicity are reduced, and the surface tension-reducing ability is lowered. Meanwhile, because the compound in which m is 3 or greater is difficult to synthesize, the synthesis cost increases.

The fluorinated imide salt compound of represented by General Formula (2) has a structure in which n is an integer from 1 to 4, and a perfluoroalkyl group having 4 or less carbon atoms is directly bonded to a sulfonic acid group of imide. Therefore, this compound has higher hydrophobicity and higher lipophobicity.

The fluorinated imide salt compound represented by General Formula (2) has a fluorocarbon group (an oxyperfluoropropylene group, an oxyperfluoropropyl group, or a perfluoroalkyl group) having a carbon chain consisting of 4 or less carbon atoms. This compound is preferable because such a compound is rapidly excreted from a living body and less bioaccumulative. Generally, the shorter the carbon chain of the fluorocarbon group is in a fluorinated compound, the lower the surface activity of the compound tends to be. The fluorinated imide salt compound of the present embodiment has the structure described above. Therefore, the compound has high surface activity even though the carbon chain of each fluorocarbon group consists of 4 or less carbon atoms.

The fluorinated imide salt compound represented by General Formula (2) has a structure in which $M^{\alpha+}$ represents an $\alpha$-valent metal ion, a primary ammonium ion, a secondary ammonium ion, a tertiary ammonium ion, or a quaternary ammonium ion. Therefore, the compound exhibits high ion dissociation properties in water. Accordingly, the compound is highly hydrophilic. In addition, because the compound has a salt structure, the compound is more stable in water.

Examples of the monovalent metal ion include a lithium ion, a sodium ion, and a potassium ion. Examples of the divalent cation include a magnesium ion and a calcium ion.

The primary ammonium ion preferably has an alkyl group having 1 to 10 carbon atoms or an aralkyl group having 6 to 10 carbon atoms. Examples of the primary ammonium ion include a methylammonium ion, an ethylammonium ion, a 1-propylammonium ion, a 2-propylammonium ion, a n-butylammonium ion, a 2-butylammonium ion, and a benzylammonium ion.

The secondary ammonium ion preferably has an alkyl group having 1 to 10 carbon atoms or an aralkyl group having 7 to 10 carbon atoms. In a case where the secondary ammonium ion has 2 alkyl groups, the 2 alkyl groups may be linked to each other to form a ring structure. The ring structure may contain an oxygen atom, a sulfur atom, a ketone group, an ester bond, or an amide bond. Examples of the secondary ammonium ion include a dimethylammonium ion, a diethylammonium ion, a di-1-propylammonium ion, a di-2-propylammonium ion, a di-n-butylammonium ion, a di-2-butylammonium ion, a dibenzylammonium ion, a benzylmethylammonium ion, a benzylethylammonium ion, a benzylpropylammonium ion, a benzylbutylammonium ion, an ethylmethylammonium ion, a methylpropylammonium ion, an ethylpropylammonium ion, a methylbutylammonium ion, an ethylbutylammonium ion, a propylbutylammonium ion, a pyrrolidinium ion, a piperidinium ion, and a morpholinium ion.

The tertiary ammonium ion preferably has an alkyl group having 1 to 10 carbon atoms or an aralkyl group having 7 to 10 carbon atoms. In a case where the tertiary ammonium ion has 2 or more alkyl groups, the 2 alkyl groups may be linked to each other to form a ring structure. The ring structure may contain an oxygen atom, a sulfur atom, a ketone group, an ester bond, or an amide bond. Examples of the tertiary ammonium ion include a trimethylammonium ion, a triethylammonium ion, a tri-1-propylammonium ion, a tri-2-propylammonium ion, a tri-n-butylammonium ion, a tri-2-butylammonium ion, a tribenzylammonium ion, a dibenzylmethylammonium ion, a dibenzylethylammonium ion, a dibenzylpropylammonium ion, a dimethylethylammonium ion, a dimethylpropylammonium ion, a dimethylbutylammonium ion, a diethylmethylammonium ion, a diethylpropylammonium ion, a diethylbutylammonium ion, a dipropylmethylammonium ion, a dipropylethylammonium ion, a dipropylbutylammonium ion, a dibutylmethylammonium ion, a dibutylethylammonium ion, a dibutylpropylammonium ion, a methylpyrrolidinium ion, an ethylpyrrolidinium ion, a methylpiperidinium ion, an ethylpiperidinium ion, a methylmorpholinium ion, and an ethylmorpholinium ion.

The quaternary ammonium ion preferably has an alkyl group having 1 to 10 carbon atoms or an aralkyl group having 7 to 10 carbon atoms. In a case where the tertiary ammonium ion has 2 or more alkyl groups, the 2 alkyl groups may be linked to each other to form a ring structure. The ring structure may contain an oxygen atom, a sulfur atom, a ketone group, an ester bond, or an amide bond. Examples of the quaternary ammonium ion include a tetramethylammonium ion, a tetraethylammonium ion, a tetra(1-propyl)ammonium ion, a tetra(2-propyl)ammonium ion, a tribenzylmethylammonium ion, a tribenzylethylammonium ion, a tribenzylpropylammonium ion, a tribenzylbutylammonium ion, a dibenzylethylmethylammonium ion, a tetra(n-butyl)ammonium ion, a tetra(2-butyl)ammonium ion, a dimethylpyrrolidinium ion, a diethylpyrrolidinium ion, an ethylmethylpyrrolidinium ion, a dimethylpiperidinium ion, a diethylpiperidinium ion, an ethylmethylpiperidinium ion, a dimethylmorpholinium ion, a diethylmorpholinium ion, and an ethylmethylmorpholinium ion.

Next, a method for manufacturing the fluorinated imide salt compound of the present embodiment will be described. A fluorinated imide metal salt compound containing an $\alpha$-valent metal ion as $M^{\alpha+}$ can be manufactured, for example, by a method in which a reaction is caused between carbonyl fluoride: $CF_3—CF_2—CF_2—O—[CF(CF_3)—CF_2—O—]_m—CF(CF_3)—COF$ and a metal salt of a perfluoroalkylsulfonamide compound: $[C_nF_{2n+1}—SO_2NH]_\alpha M_{\alpha+}$ in the presence of a fluoride: $M^1F$ and a solvent as illustrated in Reaction Formula (A).

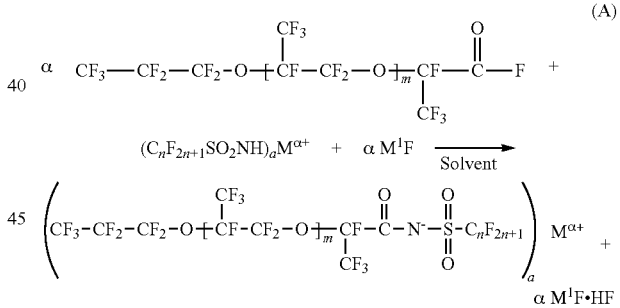

In Reaction Formula (A), m, n, and $\alpha$ have the same definitions as m, n, and $\alpha$ in General Formula (2). $M^1$ represents a monovalent cation. Examples of the monovalent cation include a hydrogen ion, a lithium ion, a sodium ion, a potassium ion, an ammonium ion, a primary ammonium ion, a secondary ammonium ion, a tertiary ammonium ion, and a quaternary ammonium ion.

Carbonyl fluoride: $CF_3—CF_2—CF_2—O—[CF(CF_3)—CF_2—O—]_m—CF(CF_3)—COF$ is a derivative of hexafluoropropylene oxide (HFPO). As this compound, commercially available products can be used. For example, as $CF_3CF_2CF_2OCF(CF_3)CF_2OCF(CF_3)COF$, it is possible to use CHEMINOX PO-3-AF marketed by Unimatec Corporation.

The metal salt of the perfluoroalkyl sulfonamide compound: $[C_nF_{2n+1}—SO_2NH]_\alpha M^\alpha$ can be manufactured, for example, by a method including a first step of causing a reaction between perfluoroalkyl sulfonyl fluoride ($C_nF_{2n+1}$—$SO_2F$) and ammonia so as to obtain a reaction solution containing an ammonium salt of perfluoroalkyl sulfonamide ($C_nF_{2n+1}$—$SO_2NH\ NH_4$) and ammonium fluoride ($NH_4F$) and a second step of causing a reaction between the reaction solution and a metal compound. As the metal compound, for example, it is possible to use at least one kind of compound selected from hydroxides, carbonates, and bicarbonates of monovalent metals (lithium, sodium, and potassium) or divalent metals (magnesium and calcium). The first step and the second step can be performed, for example, by using the method described in Japanese Patent No. 5730513.

The fluoride: $M_1F$ has an action of capturing hydrofluoric acid generated by the reaction between carbonyl fluoride and the metal salt of the perfluoroalkyl sulfonamide compound.

As the solvent, an organic solvent can be used. The organic solvent is not particularly limited as long as it does not inhibit the above reaction. For example, ethyl acetate and acetonitrile can be used.

The reaction illustrated in Reaction Formula (A) can be carried out, for example, by mixing carbonyl fluoride with the metal salt of the perfluoroalkyl sulfonamide compound in the presence of a fluoride and a solvent and stirring the mixture. As a method of mixing the carbonyl fluoride with the metal salt of the perfluoroalkyl sulfonamide compound, it is possible to use a method of adding dropwise the carbonyl fluoride to the mixed solution containing the metal salt of the perfluoroalkyl sulfonamide compound, the fluoride, and the solvent.

The reaction temperature is not particularly limited, but is preferably 70° C. or lower, and particularly preferably in a range of 0° C. to 40° C.

After the reaction ends, the fluorinated imide metal salt compound generated in the reaction solution can be isolated and purified by known methods such as extraction, filtration, and concentration.

The fluorinated imide salt compound containing a primary ammonium ion, a secondary ammonium ion, a tertiary ammonium ion, or a quaternary ammonium ion as $M^{\alpha+}$ can be manufactured as follows, for example.

First, the fluorinated imide metal salt compound containing an $\alpha$-valent metal ion as $M^{\alpha+}$ is acidolyzed using sulfuric acid or hydrochloric acid, thereby obtaining a fluorinated imide compound containing a hydrogen atom as $M^{\alpha+}$. Then, the obtained fluorinated imide compound is neutralized with an amine compound that generates a primary ammonium ion, a secondary ammonium ion, a tertiary ammonium ion, or a quaternary ammonium ion.

As the fluorinated imide salt compound of the present embodiment, for example, the following compounds are preferable.

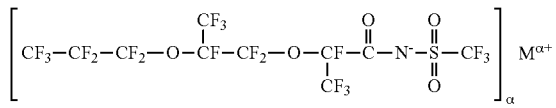  (4)

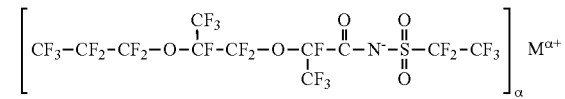  (5)

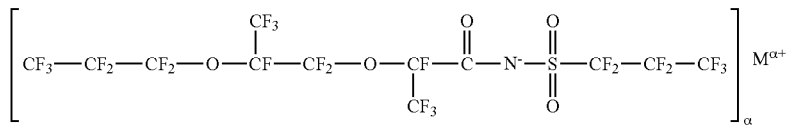  (6)

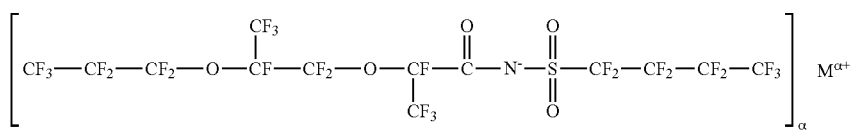  (7)

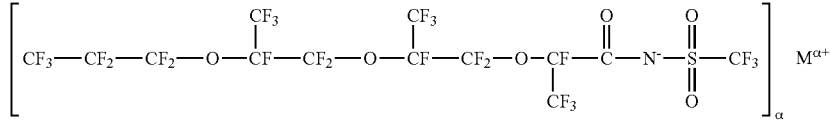  (8)

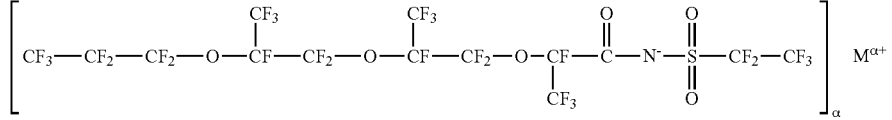  (9)

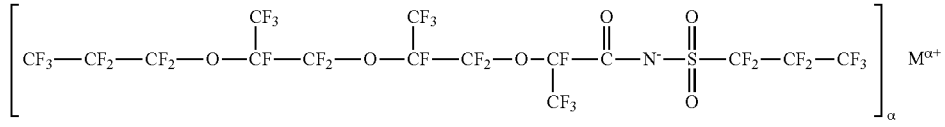  (10)

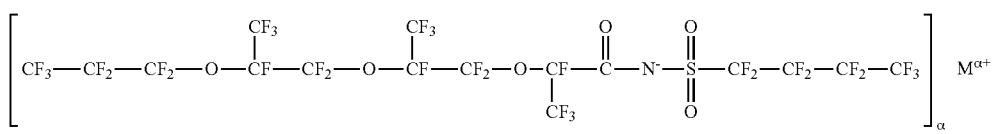

(11)

The fluorinated imide salt compound of the present embodiment contains a metal ion, a primary ammonium ion, a secondary ammonium ion, a tertiary ammonium ion, or a quaternary ammonium ion, and has an imide structure having high ion dissociation properties. Accordingly, the compound is highly hydrophilic. In addition, because the compound has a salt structure, the compound is more stable in water. In addition, the compound has a structure in which an oxyperfluoropropyl group: $[CF_3-CF_2-CF_2-O-]$ is bonded to a carboxylic acid group of imide through an oxyperfluoropropylene group: $[-CF(CF_3)-CF_2-O-]$, and a perfluoroalkyl group having 4 or less carbon atoms is directly bonded to a sulfonic acid group of imide. Therefore, the compound is highly hydrophobic and highly lipophobic. Accordingly, the fluorinated imide salt compound of the present embodiment has high solubility in an aqueous solvent or an organic solvent, exhibits excellent stability in water, and has a high surface tension-reducing ability.

Second Embodiment

The fluorinated imide salt compound according to the second embodiment of the present invention is a compound represented by General Formula (3).

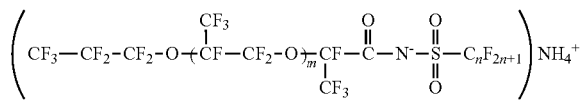

(3)

In General Formula (3), m represents 1 or 2, and n represents an integer from 1 to 4.

The structure of the fluorinated imide salt compound of the present embodiment is the same as the structure of the fluorinated imide salt compound of the first embodiment, except that the fluorinated imide salt compound of the first embodiment is a fluorinated imide ammonium salt compound in which α represents 1 and $M^{\alpha+}$ represents an ammonium ion.

The fluorinated imide ammonium salt compound of the present embodiment can be manufactured, for example, by acidolyzing a fluorinated imide metal salt compound containing an α-valent metal ion as $M^{\alpha+}$ by using sulfuric acid or hydrochloric acid so as to obtain a fluorinated imide compound containing a hydrogen atom as $M^{\alpha+}$, and then neutralizing the obtained fluorinated imide compound with ammonia.

The fluorinated imide ammonium salt compound of the present embodiment contains an ammonium ion and has an imide structure having high ion dissociation properties. Therefore, this compound is highly hydrophilic and highly stable in water. In addition, the compound has a structure in which an oxyperfluoropropyl group is bonded to a carboxylic acid group of imide through an oxyperfluoropropylene group, and a perfluoroalkyl group having 4 or less carbon atoms is directly bonded to a sulfonic acid group of imide. Therefore, the compound is highly hydrophobic and highly lipophobic. Accordingly, the fluorinated imide ammonium salt compound of the present embodiment has high solubility in an aqueous solvent or an organic solvent, exhibits excellent stability in water, and has a high surface tension-reducing ability.

<Surfactant>

The surfactant of the present embodiment contains the fluorinated imide salt compound described above. One kind of fluorinated imide salt compound may be used singly, or 2 or more kinds of fluorinated imide salt compounds may be used in combination. The surfactant of the present embodiment may contain a compound other than the fluorinated imide salt compound described above.

The surfactant of the present embodiment is easily dissolved in various products using aqueous solvents or organic solvents, for example, various coating materials or molding materials such as printing materials, photosensitive materials, photographic materials, paint, cleaning agents, optical materials, and release agents. Therefore, in these materials, the surfactant can be suitably used as an additive for enhancing permeability/wettability, leveling properties, surface functionality, and the like.

Particularly, the fluorinated imide salt compound of the first embodiment that contains a primary ammonium ion, a secondary ammonium ion, a tertiary ammonium ion, or a quaternary ammonium ion as $M^{\alpha+}$ and the fluorinated imide ammonium salt compound of the second embodiment do not contain a metal. Therefore, surfactants containing these fluorinated imide salt compounds can be advantageously used in a semiconductor manufacturing process or used as coating additives or surface treatment agents for electronic parts.

The organic solvent for dissolving the surfactant of the present embodiment is not particularly limited. Examples of the organic solvent include an alcohol such as methanol or ethanol, an ester-based solvent such as ethyl acetate, a ketone-based solvent such as acetone or N-methyl-2-pyrrolidone (NMP), an ether-based solvent such as propylene glycol monomethyl ether acetate (PGMEA) or propylene glycol monomethyl ether (PGME), an aromatic hydrocarbon-based solvent such as toluene, and a hydrocarbon-based solvent such as hexane.

The surfactant of the present embodiment contains the fluorinated imide salt compound described above. Therefore, the surfactant has a high surface tension-reducing ability. Furthermore, the surfactant of the embodiment has high solubility in an aqueous solvent or an organic solvent. Therefore the surfactant can be used for various uses.

The embodiments of the present invention have been described so far. However, the present invention is not limited thereto, and can be appropriately changed within the technical scope of the present invention.

EXAMPLES

Hereinafter, the effects of the present invention will be described with reference to examples. In the present examples, products were identified by $^{19}F$—NMR.

Example 1 of the Present Invention

A mixture (286.9 g) of $CF_3SO_2NHK$ and KF and 425 mL of acetonitrile were put into a 4-neck glass flask equipped with a reflux condenser, a thermometer, and a stirrer, and stirred so that $CF_3SO_2NHK$ was dissolved, thereby preparing a mixed solution containing dispersed KF. The mixture of $CF_3SO_2NHK$ and KF was synthesized with reference to the method described in paragraph "0067" of Japanese Patent No. 5730513 by using trifluoromethanesulfonyl fluoride ($CF_3SO_2F$) instead of heptafluoropropanesulfonyl fluoride ($C_3F_7SO_2F$).

Then, while being stirred, the prepared mixed solution was cooled with ice water, and 345.7 g of $CF_3CF_2CF_2OCF(CF_3)CF_2OCF(CF_3)COF$ (CHEMINOX PO-3-AF, Unimatec Corporation.) was added dropwise to the mixed solution for 15 minutes. After the dropping ended, the ice water was removed, and the mixed solution was stirred at room temperature for 1 hour. Thereafter, the reaction solution was filtered, KF.HF precipitated during the reaction was separated by filtration, and the obtained filtrate was concentrated using an evaporator. Ethyl acetate (180 mL) was added to the concentrated solution, and then the solution was rinsed with water 3 times. The ethyl acetate solution rinsed with water was concentrated using an evaporator, thereby obtaining a fluorinated imide potassium salt compound (369.3 g, yield: 80%) represented by Formula (12).

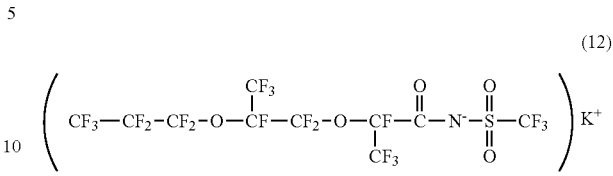

$^{19}F$—NMR ($CD_3OD$): δ−78.8 ($CF_3$, 3F), −79.4 (CF, 1F), −79.8 ($CF_3$, 3F), −80.9 ($CF_3+CF_2$, 5F), −81.7 ($CF_3$, 3F), −82.0 (CF, 1F), −128.5 (CF, 1F), −129.3 ($CF_2$, 2F), −144.4 (CF, 1F)

Example 2 of the Present Invention

A fluorinated imide potassium salt compound (yield: 71%) represented by Formula (13) was obtained in the same manner as in Example 1 of the present invention, except that a mixture of $CF_3CF_2CF_2CF_2SO_2NHK$ and KF was used instead of the mixture of $CF_3SO_2NHK$ and KF.

The mixture of $CF_3CF_2CF_2CF_2SO_2NHK$ and KF was synthesized with reference to the method described in paragraph "0067" of Japanese Patent No. 5730513 by using nonafluorobutanesulfonyl fluoride ($CF_3CF_2CF_2CF_2SO_2F$) instead of heptafluoropropanesulfonyl fluoride ($C_3F_7SO_2F$).

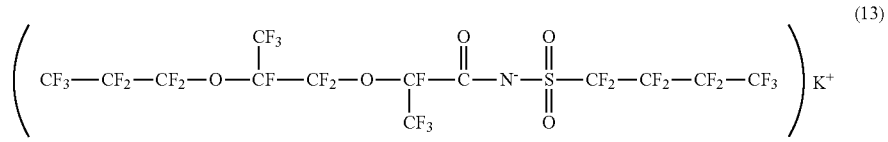

$^{19}F$—NMR ($CD_3OD$): δ−79.3 (CF, 1F), −79.9 ($CF_3$, 3F), −80.9 ($CF_3$, 3F), −81.2 ($CF_3+CF_2$, 5F), −81.6 ($CF_3$, 3F), −82.0 (CF, 1F), −113.6 ($CF_2$, 2F), −120.5 ($CF_2$, 2F), −125.6 ($CF_2$, 2F), −128.4 (CF, 1F), −129.3 ($CF_2$, 2F), −144.3 (CF, 1F)

Example 3 of the Present Invention

A fluorinated imide potassium salt compound (yield: 73%) represented by Formula (14) was obtained in the same manner as in Example 1 of the present invention, except that $CF_3CF_2CF_2OCF(CF_3)CF_2OCF(CF_3)CF_2OCF(CF_3)COF$ (manufactured by SynQuest Laboratories) was used instead of $CF_3CF_2CF_2OCF(CF_3)CF_2OCF(CF_3)COF$.

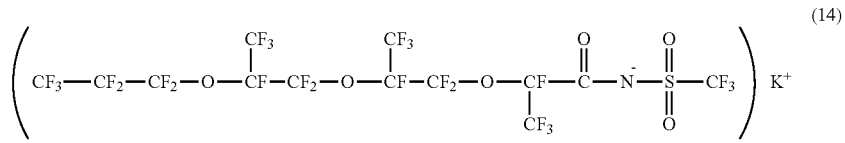

$^{19}F$—NMR ($CD_3OD$): −78.6 to −82.6 ($CF_2+CF_2+CF_2$, 6F), −78.8 ($CF_3$, 3F), −79.7 ($CF_3+CF_3$, 6F), −81.2 ($CF_3$, 3F), −81.6 ($CF_3$, 3F), −128.4 (CF, 1F), −129.3 ($CF_2$, 2F), −144.4 (CF+CF, 2F)

Example 4 of the Present Invention

The fluorinated imide potassium salt compound (300.0 g) obtained in Example 1 of the present invention and 276.3 g of concentrated sulfuric acid were put into a 4-neck glass flask equipped with a reflux condenser, a thermometer, and a stirrer, and distilled under reduced pressure while being stirred, thereby obtaining a fluorinated imide compound A represented by Formula (15) (141.4 g, yield: 50%, boiling point: 107° C. to 113° C./20 Torr)

(15)

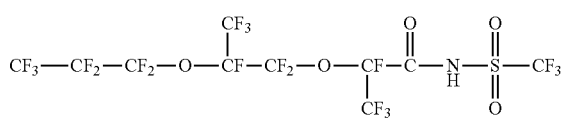

Then, 943.3 g of ultrapure water and 11.6 g of aqueous ammonia having a concentration of 25% were put into a polyethylene container having a volume of 2 L equipped with a stirrer, and 103.0 g of the fluorinated imide compound A was added dropwise through a dropping funnel to the container while being stirred so that the solution was neutralized. The obtained aqueous solution was dried in a dryer at 120° C., thereby obtaining a fluorinated imide ammonium salt compound represented by Formula (16) (104.7 g, yield: 99%).

(16)

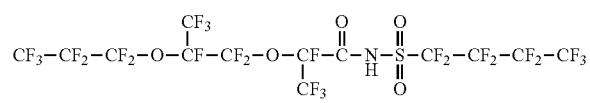

$^{19}$F—NMR (CD$_3$CN): δ−78.4 (CF$_3$, 3F), −79.5 (CF$_3$+CF, 4F), −80.7 (CF$_3$+CF$_2$, 5F), −81.3 (CF$_3$, 3F), −81.9 (CF, 1F), −127.9 (CF, 1F), −128.9 (CF$_2$, 2F), −144.3 (CF, 1F)

Example 5 of the Present Invention

A fluorinated imide compound B represented by Formula (17) (yield: 45%, boiling point 102° C. to 103° C./2 to 3 Torr) was obtained in the same manner as in Example 4 of the present invention, except that the fluorinated imide potassium salt compound obtained in Example 2 of the present invention was used instead of the fluorinated imide potassium salt compound obtained in Example 1 of the present invention.

(17)

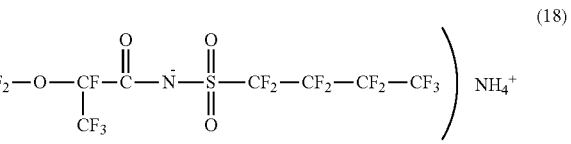

Then, a fluorinated imide ammonium salt compound (yield: 99%) represented by Formula (18) was obtained in the same manner as in Example 4 of the present invention, except that the fluorinated imide compound B was used instead of the fluorinated imide compound A.

(18)

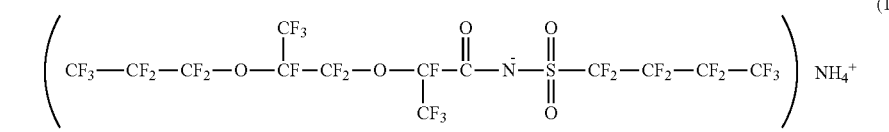

$^{19}$F—NMR (CD$_3$CN): δ−79.5 (CF, 1F), −79.5 (CF$_3$, 3F), −80.4 (CF$_3$, 3F), −80.8 (CF$_3$+CF$_2$, 5F), −81.3 (CF$_3$, 3F), −81.5 (CF, 1F), −113.6 (CF$_2$, 2F), −120.6 (CF$_2$, 2F), −125.3 (CF$_2$, 2F), −127.8 (CF, 1F), −128.9 (CF$_2$, 2F), −144.3 (CF, 1F)

Example 6 of the Present Invention

A fluorinated imide triethylammonium salt compound (yield: 99%) represented by Formula (19) was obtained in the same manner as in Example 4 of the present invention, except that triethylamine was used instead of the aqueous ammonia having a concentration of 25%.

(19)

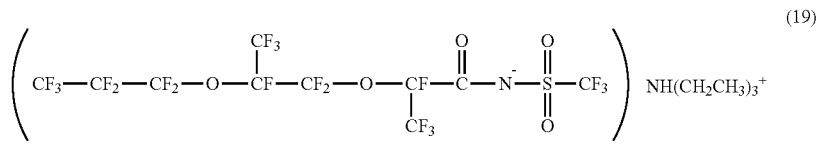

$^{19}$F—NMR (CD$_3$CN): δ–78.7 (CF$_3$, 3F), –79.6 (CF$_3$+CF, 4F), –80.9 (CF$_3$+CF$_2$, 5F), –81.4 (CF$_3$, 3F), –81.8 (CF, 1F), –127.8 (CF, 1F), –129.0 (CF$_2$, 2F), –144.4 (CF, 1F)

Example 7 of the Present Invention

A fluorinated imide tetramethylammonium salt compound (yield: 99%) represented by Formula (20) was obtained in the same manner as in Example 4 of the present invention, except that tetramethylammonium hydroxide (10% aqueous solution) was used instead of the aqueous ammonia having a concentration of 25%.

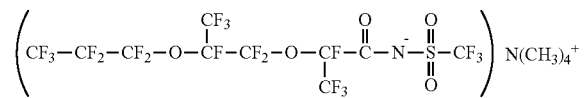

(20)

$^{19}$F—NMR (CD$_3$CN): δ–78.7 (CF$_3$, 3F), –79.6 (CF$_3$+CF, 4F), –80.9 (CF$_3$+CF$_2$, 5F), –81.4 (CF$_3$, 3F), –81.8 (CF, 1F), –127.8 (CF, 1F), –129.0 (CF2, 2F), –144.4 (CF, 1F)

Comparative Example 1

A commercially available bis(perfluorobutanesulfonyl) imide potassium salt: (C$_4$F$_9$SO$_2$)$_2$N.K$^+$(manufactured by TOKYO CHEMICAL INDUSTRY CO., LTD.) was prepared.

Comparative Example 2

A commercially available potassium salt of perfluorooctanesulfonic acid (PFOS) (manufactured by TOKYO CHEMICAL INDUSTRY CO., LTD.) was prepared.

Comparative Example 3

A fluorinated imide potassium salt compound (yield: 73%) represented by Formula (21) was obtained in the same manner as in Example 1 of the present invention, except that CF$_3$CF$_2$CF$_2$OCF(CF$_3$)COF (CHEMINOX PO-2-AF, Unimatec Corporation.) was used instead of CF$_3$CF$_2$CF$_2$OCF(CF$_3$)CF$_2$OCF(CF$_3$)COF.

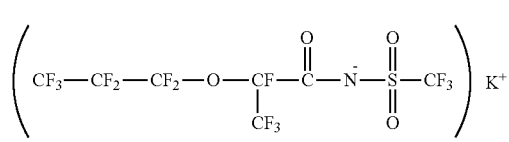

(21)

Comparative Example 4

A fluorinated imide potassium salt compound (yield: 71%) represented by Formula (22) was obtained in the same manner as in Example 1 of the present invention, except that a mixture of CF$_3$CF$_2$SO$_2$NHK and KF was used instead of the mixture of CF$_3$SO$_2$NHK and KF and that CF$_3$CF$_2$CF$_2$OCF(CF$_3$)COF (CHEMINOX PO-2-AF, Unimatec Corporation.) was used instead of CF$_3$CF$_2$CF$_2$OCF(CF$_3$)CF$_2$OCF(CF$_3$)COF.

The mixture of CF$_3$CF$_2$SO$_2$NHK and KF was synthesized with reference to the method described in paragraph "0067" of Japanese Patent No. 5730513 by using pentafluoroethanesulfonyl fluoride (CF$_3$CF$_2$SO$_2$F) instead of heptafluoropropanesulfonyl fluoride (C3F7SO$_2$F).

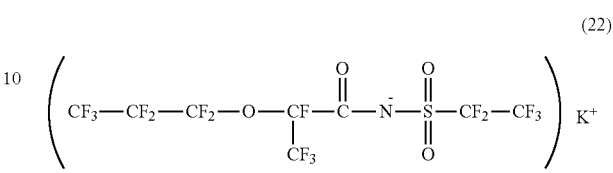

(22)

Comparative Example 5

The fluorinated imide compound A obtained in Example 4 of the present invention was used.

[Evaluation]

The surface activity of the compounds obtained in Examples 1 to 7 of the present invention and Comparative Examples 1 to 5 and the stability of the compounds in water were evaluated.

(Surface Activity)

Each of the compounds was mixed with water so that an aqueous solution having a concentration of 1,000 ppm by mass was prepared. By measuring the surface tension of the prepared aqueous solution, the surface activity was evaluated. The surface tension was measured by the Wilhelmy method using an automatic surface tensiometer CBVP-Z manufactured by Kyowa Interface Science Co., LTD. The measurement results are shown in the following Table 1. The potassium salt of PFOS of Comparative Example 2 formed a saturated aqueous solution without being completely dissolved in water. Therefore, in Comparative Example 2, the surface tension was measured in the saturated state.

(Stability in Water)

Each of the compounds was mixed with water so that an aqueous solution having a concentration of 10% by mass was prepared. The prepared aqueous solution was stored for 20 days in a room adjusted to 20° C. to 25° C. By calculating a decomposition rate of the compound from $^{19}$F—NMR spectra of the compound in the aqueous solution that were obtained before and after the storage, the stability in water was evaluated. The decomposition rate was calculated by the following formula. A compound having a decomposition rate of 3% or less was described as "No decomposition". The measurement results are shown in the following Table 1. The potassium salt of PFOS of Comparative Example 2 formed a saturated aqueous solution without being completely dissolved in water. Therefore, in Comparative Example 2, the stability in water was evaluated in the saturated state.

Decomposition rate (%)={1-(integration value of $^{19}$F—NMR spectrum after storage/integration value of $^{19}$F—NMR spectrum before storage)}× 100

TABLE 1

| | Surface tension (mN/m) | Stability in water |
|---|---|---|
| Example 1 of the present invention | 24 | No decomposition |
| Example 2 of the present invention | 17 | No decomposition |
| Example 3 of the present invention | 16 | No decomposition |
| Example 4 of the present invention | 24 | No decomposition |

TABLE 1-continued

| | Surface tension (mN/m) | Stability in water |
|---|---|---|
| Example 5 of the present invention | 18 | No decomposition |
| Example 6 of the present invention | 24 | No decomposition |
| Example 7 of the present invention | 23 | No decomposition |
| Comparative Example 1 | 43 | No decomposition |
| Comparative Example 2 | 41 (saturated) | No decomposition |
| Comparative Example 3 | 55 | No decomposition |
| Comparative Example 4 | 50 | No decomposition |
| Comparative Example 5 | 18 | 30% decomposition |

It has been revealed that the fluorinated imide salt compounds of Examples 1 to 7 of the present invention have a higher surface tension-reducing ability, compared to the conventional fluorinated compounds, such as bis(perfluorobutanesulfonyl)imide potassium salt of Comparative Example 1 and perfluorooctanesulfonic acid (PFOS) of Comparative Example 2, and the fluorinated imide salt compounds of Comparative Examples 3 and 4 in which oxyperfluoropropyl group is bonded to a carboxylic acid group of imide without the intervention of an oxyperfluoropropylene group.

Furthermore, it has been revealed that the fluorinated imide salt compounds of Examples 1 to 7 of the present invention are more stable in water, compared to the fluorinated imide compound of Comparative Example 5 which does not have a salt structure.

What is claimed is:

1. A fluorinated imide salt compound represented by General Formula (1),

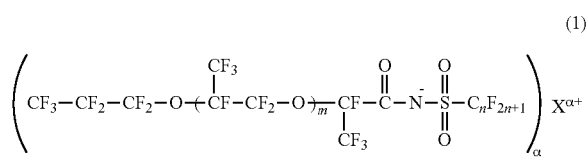

(1)

in General Formula (1), m represents 1 or 2, n represents an integer from 1 to 4, α represents 1 or 2, and $X^{\alpha+}$ represents an α-valent metal ion, a primary ammonium ion, a secondary ammonium ion, a tertiary ammonium ion, a quaternary ammonium ion, or $NH_4^+$.

2. The fluorinated imide salt compound according to claim 1 represented by General Formula (2),

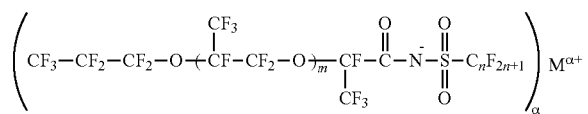

(2)

in General Formula (2), m represents 1 or 2, n represents an integer from 1 to 4, a represents 1 or 2, and $M^{\alpha+}$ represents an α-valent metal ion, a primary ammonium ion, a secondary ammonium ion, a tertiary ammonium ion, or a quaternary ammonium ion.

3. The fluorinated imide salt compound according to claim 1 represented by General Formula (3),

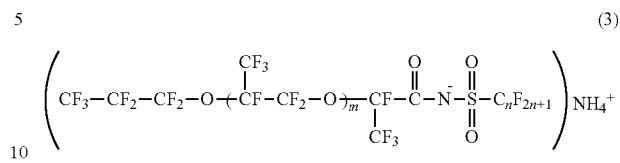

(3)

in General Formula (3), m represents 1 or 2, and n represents an integer from 1 to 4.

4. A surfactant comprising the fluorinated imide salt compound represented by General Formula (1),

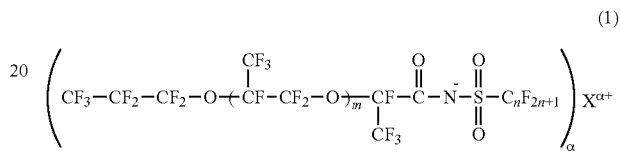

(1)

in General Formula (1), m represents 1 or 2, n represents an integer from 1 to 4, α represents 1 or 2, and $X^{\alpha+}$ represents an α-valent metal ion, a primary ammonium ion, a secondary ammonium ion, a tertiary ammonium ion, a quaternary ammonium ion, or $NH_4^+$.

5. The surfactant according to claim 4,
wherein the fluorinated imide salt compound is represented by General Formula (2),

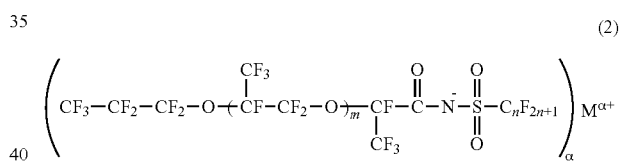

(2)

in General Formula (2), m represents 1 or 2, n represents an integer from 1 to 4, α represents 1 or 2, and $M^{\alpha+}$ represents an α-valent metal ion, a primary ammonium ion, a secondary ammonium ion, a tertiary ammonium ion, or a quaternary ammonium ion.

6. The surfactant according to claim 4,
wherein the fluorinated imide salt compound is represented by General Formula (3),

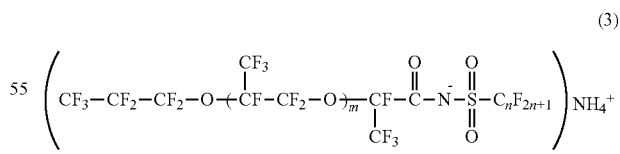

(3)

in General Formula (3), m represents 1 or 2, and n represents an integer from 1 to 4.

* * * * *